(12) United States Patent
Higuchi et al.

(10) Patent No.: US 6,238,626 B1
(45) Date of Patent: May 29, 2001

(54) AUTOMATIC DISTRIBUTION APPARATUS AND METHOD OF DISTRIBUTION

(75) Inventors: Akira Higuchi; Eiji Watanabe, both of Fukuoka; Naoki Miyazaki, Saga; Kanji Yahiro, Fukuoka; Kenichi Kuroda, Fukuoka; Hideyoshi Kitahara, Fukuoka; Kenji Ishiyama, Fukuoka; Takashi Daikoku, Fukuoka, all of (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/289,607

(22) Filed: Apr. 12, 1999

(30) Foreign Application Priority Data

Apr. 13, 1998 (JP) .................................. 10-100767

(51) Int. Cl.⁷ ..................................................... B01L 3/02
(52) U.S. Cl. ............................ 422/100; 422/99; 422/104; 422/65; 436/180; 73/863.32; 73/864.14; 73/864.24
(58) Field of Search ............................ 422/99, 100, 104, 422/65; 73/863.01, 863.31, 863.32, 864, 864.02, 864.24, 864.14, 864.25; 436/180, 47; 141/130

(56) References Cited

U.S. PATENT DOCUMENTS 4,478,094 * 10/1984 Salomaa et al. .................. 73/863.32
5,039,615 * 8/1991 Takahata ............................... 436/44
5,102,623 * 4/1992 Yamamoto et al. .................... 422/63
5,273,717 * 12/1993 Marvin ................................. 422/100
5,363,885 * 11/1994 McConnell et al. ..................... 141/1

* cited by examiner

Primary Examiner—Jill Warden
Assistant Examiner—Keith Bex
(74) Attorney, Agent, or Firm—Wenderoth, Lind & Ponack, L.L.P.

(57) ABSTRACT

In a method for distributing liquids, in which a distribution tip attached detachably to the lower end of a distribution nozzle can be replaced at any time necessary, a tip rack having a plurality of unused distribution tips lined up thereon is placed on a fitting stage to have the distribution tips fitted with a distribution nozzles. Then, the existence, or non-existence, of a distribution tip left behind on the tip rack without being attached to a distribution nozzle after the fitting operation is finished is detected by a detection section formed of an interrupting-type light sensor, the targeted place of detection by the light sensor being the lower end of the distribution tip. Under the above-described structure, misfitting of a distribution tip can be detected with a high certainty at an early stage before an operation for sucking/discharging liquids is started.

10 Claims, 3 Drawing Sheets

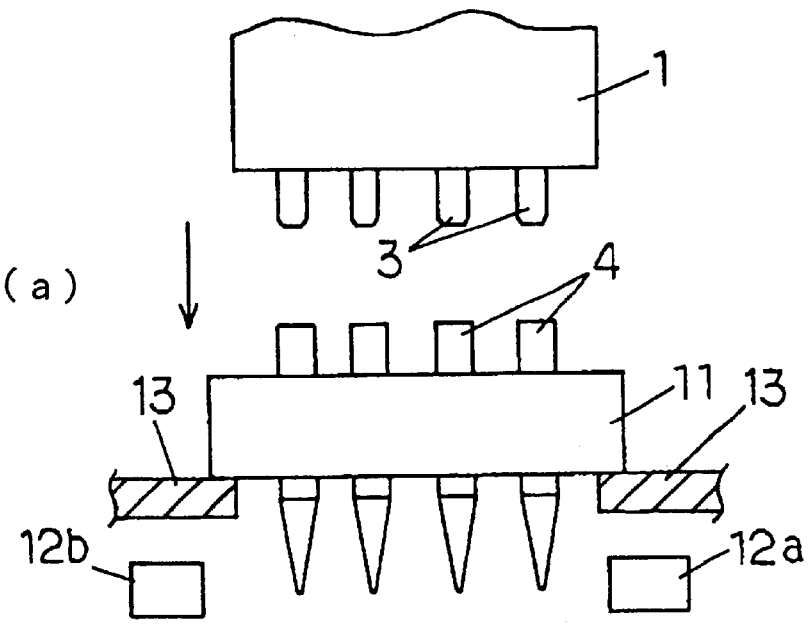
F I G. 3 (a)
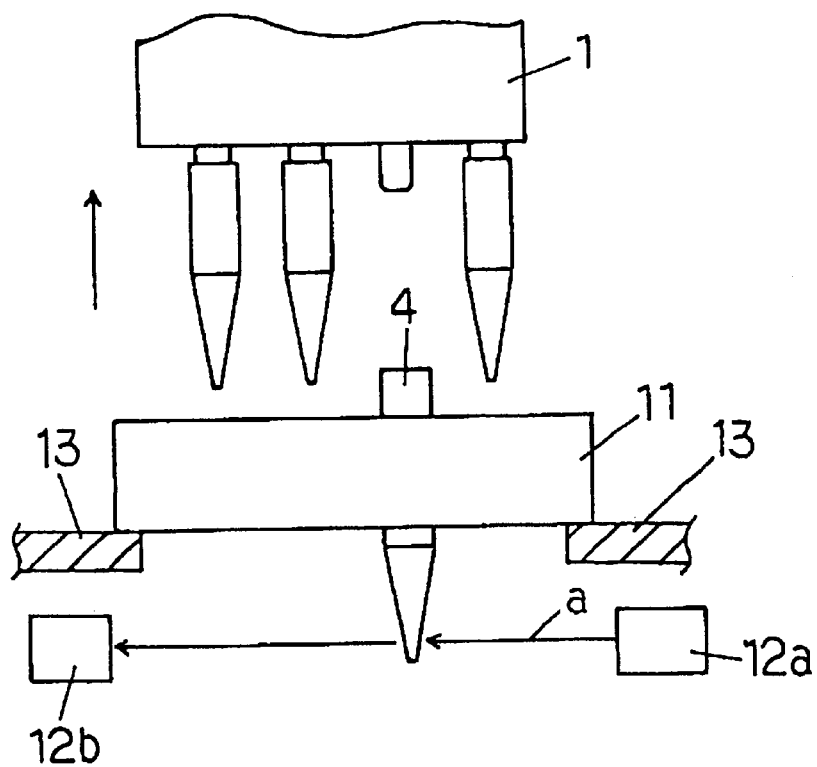
F I G. 3 (b)

AUTOMATIC DISTRIBUTION APPARATUS AND METHOD OF DISTRIBUTION

FIELD OF THE INVENTION

The present invention relates to an automatic distribution apparatus and a method of distributing samples or reagents used in biochemical and the like fields.

BACKGROUND OF THE INVENTION

Distributing liquid samples or reagents to a plurality of sample vessels in small quantities is an indispensable operation during experiment or analysis activities in the biochemical field, for example. The distribution is performed by sucking/discharging liquid through a distribution nozzle. The distribution nozzle is normally fitted with a disposable distribution tip. The distribution tip is replaced with a new one at any time whenever necessary.

A distribution tip is fitted to the distribution nozzle by inserting the lower end of the latter into a pipet-shaped distribution tip. The firmness of fitting depends solely on the elastic fastening force of a resin distribution tip surrounding the lower end portion of the distribution nozzle. Because of dimensional dispersions in the inner diameters of distribution tips, the fastening forces sometimes fall short of a level required to insure a normal fitting state. This invites a misfitted state with the distribution tip.

During a distribution operation, if a distribution head proceeds without having a distribution tip perfectly fitted thereto, a receiving plate will have a portion void of sample liquid. For assuring reliability of the test result, misfitting of a distribution tip should be avoided by all means. In a conventional apparatus, where a single distribution tip is used, the existence, or non-existence, of a distribution tip may be checked upon through an electrical conductivity test using a conductive material for the distribution tip. Or, it may be confirmed indirectly by watching a pressure during a suction operation. The above-described checking methods, however, are hardly applicable to a distribution head that has multiple distribution tips. The problem with the conventional automatic distribution apparatus is that it is difficult to detect a misfitted distribution tip with a high certainty level.

SUMMARY OF THE INVENTION

An automatic distribution apparatus for distributing liquid is designed such that a distribution tip attached detachably to the lower end of a distribution nozzle can be replaced at any time whenever necessary. The automatic distribution apparatus comprises a fitting stage that supports a holding member holding a plurality of unused distribution tips lined up thereon to have the unused distribution tips fitted to respective distribution nozzles, and detection means for detecting, after a fitting operation is finished, whether or not there is a distribution tip left behind on the holding member without being attached to a distribution nozzle. In a distribution apparatus having the above-described structure, misfitting of a distribution tip can be detected with a high certainty level at an early stage before the apparatus proceeds to a suction/discharge operation.

An invented distribution apparatus further comprises a light sensor, whose optical axis is in parallel with the aligning line of distribution tips disposed on the holding member. This further improves the accuracy of detection.

BRIEF DESCRIPTION OF THE DRAWINGS

FIG. 3($a$) is a drawing used to show an operation of the detection section of the automatic distribution apparatus.

FIG. 3($b$) is another drawing used to show an operation of the detection section.

DESCRIPTION OF PREFERRED EMBODIMENTS

Exemplary embodiments of the present invention are described below with reference to the drawings.

Figure 1:
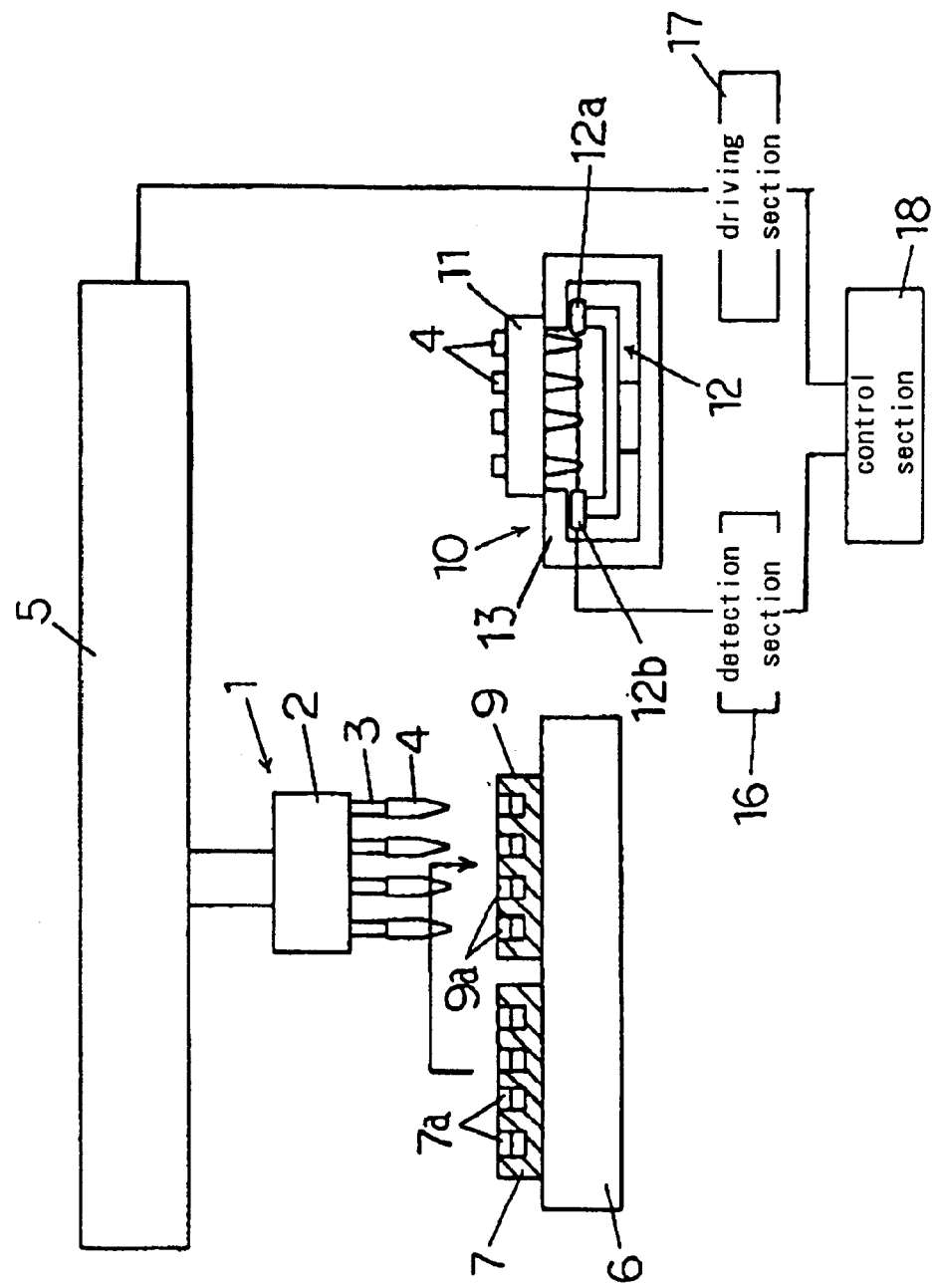
FIG. 1 shows a side view of an automatic distribution apparatus in accordance with an exemplary embodiment of the present invention.

The structure of an invented automatic distribution apparatus is described referring to FIG. 1. A nozzle holder 2 of a distribution head 1 comprises a plurality of distribution nozzles 3. Each of the distribution nozzles 3 is fitted with a distribution tip 4. The distribution head 1 can be moved in horizontal directions (X Y directions) by transfer means, or an X Y table 5.

Within a movement range of the distribution head 1, a distribution stage 6 is provided. The distribution stage 6 has a reserver 7 and a microplate 9 provided thereon. The distribution head 1 is shifted to a position so that the bottom end of the distribution tips 4 fitted to the distribution nozzles 3 can dip into in a small hollow 7$a$ of the reserver 7, and liquid kept within the small hollows 7$a$ is sucked up through the bottom ends of the distribution tips 4. Then, the distribution head 1 is shifted to a position above the microplate 9, at a place where the distribution nozzles 3 face a small hollow 9$a$ of the microplate 9, and then the distribution nozzle 3 is lowered so that the bottom ends of the distribution tips 4 dip into the small hollows 9$a$ for discharging the liquid being sucked within the distribution tips 4 into the small hollows 9$a$.

A fitting stage 10 for fitting the distribution tips 4 is provided at a place within the movement range of the distribution head 1. A tip rack 11 for holding the distribution tips 4 is placed on the fitting stage 10. On the tip rack 11 are multiple distribution tips 4 disposed vertically, lined up in correspondence with the orientation of the distribution nozzles 3. The distribution head 1 is shifted to a place above the fitting stage 10, with the distribution nozzles 3 aligned with the distribution tips 4. By lowering the distribution head 1, the distribution nozzles 3 are fitted at the lower ends an unused distribution tips 4.

Figure 2:
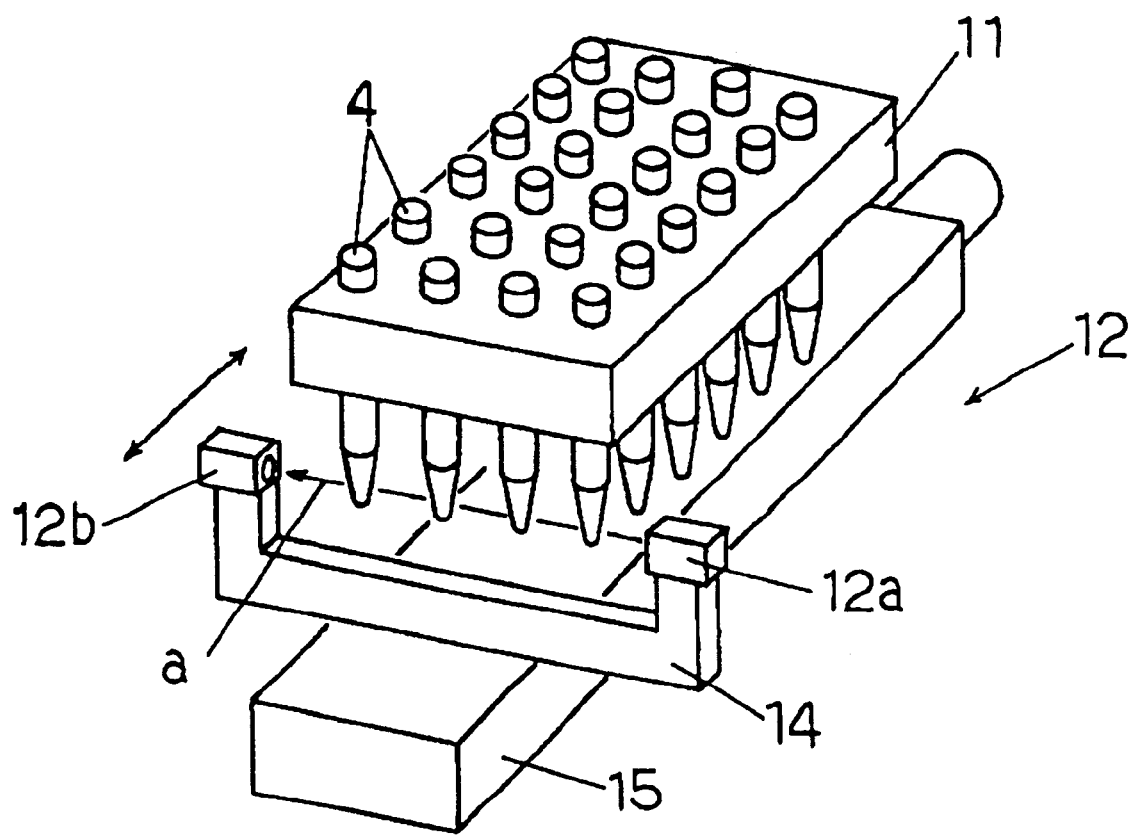
FIG. 2 is a perspective view showing a detection section of the automatic distribution apparatus.

Now in the following, means for detecting the distribution tips is described referring to FIG. 1 and FIG. 2. As shown in FIG. 1, a light sensor 12 is provided beneath the tip rack 11 mounted on a table 13 of the fitting stage 10. The light sensor 12 is an interruption type light sensor comprising a light emitting section 12$a$ and a light sensing section 12$b$. The height of an optical axis "a" has been adjusted so as to hit the bottom ends of the distribution tips 4 projecting downward from the lower edge of the tip rack 11, as shown in FIG. 2. The optical axis "a" of the light sensor 12 extends in parallel with the queue line formed of the distribution tips 4 being held on the tip rack 11. Whether any of the distribution tips 4 of each queue is in the optical axis "a", or not, can be detected at a detection section 16 by sensing the light emitted from the light emitting section 12$a$ in the light sensing section 12$b$. The results of sensing are delivered to a control section 18. The control section 18 drives the X Y table 5, via a driving section 17, to perform specific operations, such as re-fitting, discarding, etc. of distribution tip 4, in accordance with the results of sensing.

The light emitting section 12$a$ and the light sensing section 12$b$ have been installed on a bracket 14 mounted on a transfer mechanism, or a movable table 15. When the movable table 15 is moved, the optical axis "a" shifts relative to the tip rack 11 in a horizontal direction perpendicular to the optical axis "a", in order to detect the existence, or non-existence, of a distribution tip 4 in each of the queues of distribution tips 4 on the tip rack 11.

The operation of an automatic distribution apparatus having the above structure is described in the following. As shown in FIG. 1, a tip rack 11 carrying unused distribution tips 4 is brought from a stock section (not shown) to be placed on the fitting stage 10. Distribution head 1, from which the used distribution tips 4 have already been removed, is located in a place above the tip rack 11. The positions of distribution nozzles 3 are aligned to be located just above the distribution tips 4. Then, as shown in FIG. 3(a), the distribution head 1 is lowered to have the bottom ends of distribution nozzles 3 inserted into the distribution tips 4. The distribution tip 4 are thus fitted to the distribution nozzles 3. After that, the distribution head 1 is raised upward, as illustrated in FIG. 3(b). Due to dimensional dispersions among the distribution tips 4, there may be a case where one or more of the distribution tips 4 are not fitted firmly with the distribution nozzles 3 to establish a normal fitting state. Such a distribution tip remains on the tip rack 11.

In order to detect such a remaining distribution tip 4, the location of the optical axis "a" of light sensor 12 is adjusted to coincide with each of the respective queues of the distribution tips 4. By measuring the amount of light emitted from the light emitting section 12a received at the light sensing section 12b, the existence, or non-existence, of a distribution tip 4 remaining in the optical axis "a", namely the one kept staying in the tip rack 11, can be detected at the detection section 16. Such a distribution tip 4 remaining in the tip rack 11 without being attached to the distribution nozzle 3 can be thoroughly detected by shifting, through driving of movable table 15, the location of optical axis "a" to check; one after another, all of the queues of the distribution tips 4.

The targeted point of detection by the optical axis "a" is at the bottom end of the distribution tips 4 projecting downward from the lower edge of the tip rack 11. Therefore, as soon as the distribution head 1 starts making an upward motion, after having been fitted with the distribution tips; the misfitting of a distribution tip 4 with a distribution nozzle 3 is immediately detected at each of the fitting operation cycles. The early detection of misfitting reduces lost time, which would have otherwise been consumed in vain in an unfruitful motion for starting a distribution operation without correcting the misfitting. Without wasting time, an appropriate correction measure that suits best to the general circumstance of respective cases can be selected among the choices exemplified below.

In a case in which there is no problem in the dimensional accuracy and the quality of the distribution tip 4, and thus the misfitting is considered to have been caused by a reason outside the distribution tip 4, the distribution head 1 is lowered once again for fitting. The remaining distribution tip 4 may be attached to the distribution nozzle 3. If misfitting occurs repeatedly for a certain specified number of times, then the distribution tip is judged to be rejected, and the tip rack concerned is replaced with a new tip rack.

In a case in which the dimensional dispersions among distribution tips 4 are evident and the misfitting seems to occur at a certain frequency, then all the relevant distribution tips 4 are rejected as soon as misfitting first occurs. A new tip rack 11 is introduced. The above described may be another choice.

As still another choice, a distribution head 1 that caused misfitting may be inspected by the hands of engineers for correcting the misfitting of the distribution tip 4. In any of the cases, countermeasures against the misfitting can be taken before the next operational step for sucking/discharging liquid starts. If a distribution head void of a distribution tip conducts a sucking/discharging operation, the relevant plate can not serve as a due sample. In accordance with the present invention, the time loss and/or material loss due to misfitting can be minimized.

As described in the foregoing, the present invention has made it possible to detect the existence, or non existence, of a distribution tip left behind on a holding member (on tip rack) because it remains unattached to a distribution nozzle after a fitting operation is finished. Thus the misfitting of a distribution tip is detected with a high certainty level at an early stage before it proceeds to a step of suction/discharge operations. Possible losses to be caused by misfitting can be reduced to a minimum in terms of both the time and the material.

What is claimed is:

1. An automatic distribution apparatus for distributing liquids, wherein a distribution tip attached to a lower end of a distribution nozzle can be replaced at any time necessary, comprising:

a fitting stage that supports a tip rack for holding a plurality of unused distribution tips lined up thereon with lower ends of the unused distribution tips projecting downward from a bottom of the tip racks to have the plurality of unused distribution tips fitted with the distribution nozzles; and a detector for detecting whether or not there is a distribution tip left behind on the tip rack without being attached to one of the distribution nozzles after a fitting operation is finished;

wherein a targeted place of detection by said detector is a portion, of the unused distribution tip left behind on the tip rack, which projects downward from the bottom of the tip rack.

2. The automatic distribution apparatus of claim 1, wherein said detector comprises an optical device for detecting the distribution tip left behind on the tip rack.

3. The automatic distribution apparatus of claim 1, wherein said detector comprises a light sensor having an optical axis in parallel with a direction of the unused distribution tips when lined up on the tip rack.

4. The automatic distribution apparatus of claim 3, further comprising a transfer mechanism for moving the optical axis relative to the tip rack in a direction perpendicular to the optical axis.

5. The automatic distribution apparatus recited in claim 1, wherein said detector has an optical axis arranged below the tip rack.

6. A method of distributing liquids, wherein a distribution tip, which is attached to a lower end of a distribution nozzle, can be replaced at any time necessary, comprising:

placing a tip rack holding a plurality of unused distribution tips lined up thereon with lower ends of the unused distribution tips projecting downward from a bottom of the tip rack;

fitting said plurality of unused distribution tips with said distribution nozzles; and then detecting whether or not there is a distribution tip left behind on said tip rack without being attached to said distribution nozzle, by detecting a portion, of the distribution tip left behind, which is projecting downward from the bottom of said tip rack.

7. The distribution method recited in claim 6, wherein said detecting comprises optically detecting said distribution tip left behind.

8. The distribution method recited in claim 7, wherein, in optically detecting said distribution tip left behind, a light sensor is arranged with its optical axis in parallel with a direction of the distribution tips lined up on said tip rack.

9. The distribution method recited in claim 8, further comprising shifting a location of said optical axis relative to said tip rack in a direction perpendicular to the optical axis.

10. The distribution method recited in claim 6, further comprising rejecting all of the plurality of unused distribution tips fitted with said distribution nozzles, after detecting the distribution tip left behind on said tip rack.

* * * * *